(12) United States Patent
Nanaumi (10) Patent No.: US 10,064,558 B2
(45) Date of Patent: *Sep. 4, 2018

(54) SUBJECT INFORMATION ACQUISITION DEVICE, METHOD FOR CONTROLLING SUBJECT INFORMATION ACQUISITION DEVICE, AND STORAGE MEDIUM STORING PROGRAM THEREFOR

(71) Applicant: CANON KABUSHIKI KAISHA, Tokyo (JP)

(72) Inventor: Ryuichi Nanaumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,925

(22) Filed: Mar. 23, 2017

(65) Prior Publication Data

US 2017/0188840 A1 Jul. 6, 2017

Related U.S. Application Data

(63) Continuation of application No. 14/092,017, filed on Nov. 27, 2013, now Pat. No. 9,636,022.

(30) Foreign Application Priority Data

Dec. 4, 2012 (JP) .................... 2012-265322

(51) Int. Cl.
*A61B 5/00* (2006.01)

(52) U.S. Cl.
CPC .......... *A61B 5/0095* (2013.01); *A61B 5/7235* (2013.01); *A61B 5/742* (2013.01)

(58) Field of Classification Search
CPC ...... A61B 5/0095; A61B 5/7235; A61B 5/742
See application file for complete search history.

(56) References Cited

U.S. PATENT DOCUMENTS 5,640,959 A * 6/1997 Hara .................... G01N 29/262
600/447
5,713,356 A * 2/1998 Kruger ................. A61B 5/0091
600/407

(Continued)

OTHER PUBLICATIONS

Xu et al. "Universal back-projection for photoacoustic computed tomography". Physical Review E 71, 016706 (2005).*

(Continued)

*Primary Examiner* — Michael Rozanski
(74) *Attorney, Agent, or Firm* — Canon USA Inc., IP Division (57) ABSTRACT

A subject information acquisition device includes an elastic wave receiving unit configured to receive elastic waves generated inside a subject and output a reception signal; and a signal processing unit configured to acquire subject information in an interest region of the subject, on the basis of the reception signal. In measurement states, the elastic wave receiving unit receives elastic waves and outputs reception signals corresponding to the measurement states. The signal processing unit corrects the reception signals by weighting factors based on measurement parameters in the measurement states, and acquires corrected reception signals in the interest region corresponding to the measurement states. The signal processing unit acquires the subject information in the interest region, on the basis of the sum of the corrected reception signals and the sum of the weighting factors.

18 Claims, 7 Drawing Sheets

(56) References Cited

U.S. PATENT DOCUMENTS

| 9,636,022 B2* | 5/2017 | Nanaumi | A61B 8/4209 |
| 2008/0306371 A1* | 12/2008 | Fukutani | A61B 5/0059 |
| | | | 600/407 |
| 2011/0128816 A1* | 6/2011 | Baba | A61B 5/0073 |
| | | | 367/11 |

OTHER PUBLICATIONS

Manohar et al. "Initial results of in vivo non-invasive cancer imaging in the human breast using near-infrared photoacoustics". Optics Express vol. 15, No. 19. 2007.*

* cited by examiner

SUBJECT INFORMATION ACQUISITION DEVICE, METHOD FOR CONTROLLING SUBJECT INFORMATION ACQUISITION DEVICE, AND STORAGE MEDIUM STORING PROGRAM THEREFOR

CROSS-REFERENCE TO RELATED APPLICATIONS

This application is a Continuation of U.S. patent application Ser. No. 14/092,017 filed Nov. 27, 2013, now U.S. Pat. No. 9,636,022, which claims foreign priority benefit of Japanese Patent Application No. 2012-265322, filed Dec. 4, 2012. The disclosures of the above-named applications are hereby incorporated by reference herein in their entirety.

BACKGROUND OF THE INVENTION

Field of the Invention

The present invention relates to a subject information acquisition device for receiving elastic waves generated inside the subject, and acquiring subject information.

Description of the Related Art

As one of in vivo imaging techniques using near-infrared light, photo acoustic imaging (PAI) is known. General principles of photo acoustic imaging will be explained below in detail.

By irradiating a subject, such as a living body, with pulsed light generated from a light source, light which is propagated and diffused within the subject is absorbed with a light absorption body, and photo acoustic waves are generated. The principle of generation of the photo acoustic waves is known as the photo acoustic effect. In a living body, not all tissues absorb light in the same manner. A tumor's absorption of light energy in near-infrared light is higher than surrounding tissues. Therefore, a tumor that absorbs more light than surrounding tissues, instantly expands, and generates photo acoustic waves.

In photo acoustic imaging, the photo acoustic waves are received by a transducer, and by signal-processing the received signal (image reconstruction), information such as spatial distribution of the initial sound pressure of photo acoustic waves that occur upon absorption of light energy in the subject is turned into images. The spatial distribution of sound pressure generated is related to an absorption coefficient of light. Therefore, diagnosing a subject using a spatial distribution related to the absorption coefficient of light is being studied.

As an example of photo acoustic imaging, Non-Patent Literature 1 (Minghua Xu and Lihong V. Wang, "Universal back-projection algorithm for photoacoustic computed tomography", PHYSICAL REVIEW E 71, 016706 (2005)) discloses a photo acoustic imaging technique which calculates initial sound pressure of photo acoustic waves by image reconstruction by time-domain back projection.

Figure 8:
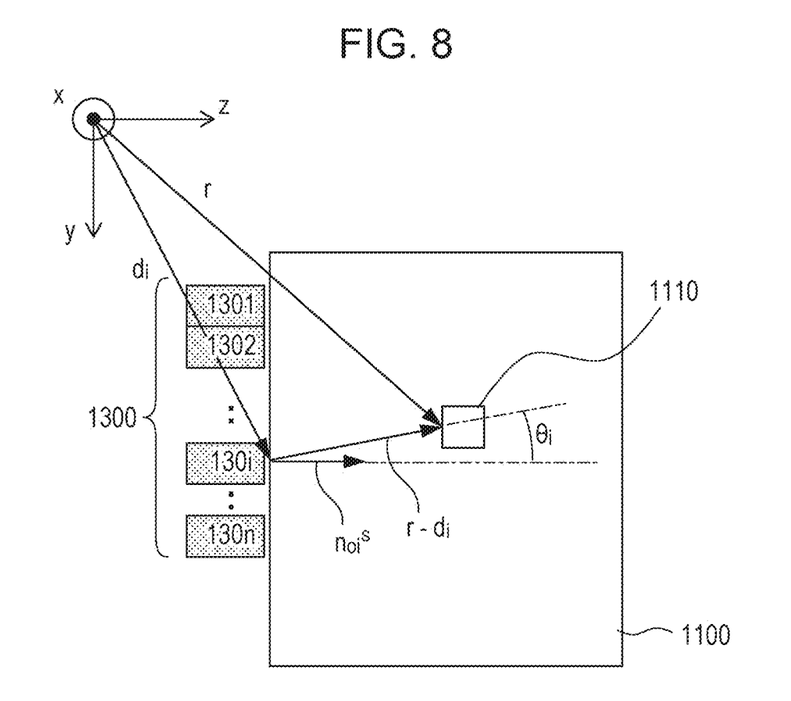
FIG. 8 is a diagram illustrating a subject information acquisition device according to related art.

Hereinafter, the image reconstruction method disclosed in Non-Patent literature 1 will be explained with reference to FIG. 8. FIG. 8 illustrates a block diagram in which an array transducer 1300 receives photo acoustic waves generated in an interest region 1110 within a subject 1100. The array transducer 1300 includes n transducers 1301 to 130$n$ arranged one-dimensionally.

Non-Patent Literature 1 discloses to acquire the initial sound pressure $p_0$ in the interest region 1110 by the time-domain back projection represented by formula (1).

$$p_0(r) = \sum_{i=1}^{n} \Delta\Omega_i \times b\left(d_i, \frac{|d_i - r|}{v}\right) \bigg/ \sum_{i=1}^{n} \Delta\Omega_i \qquad \text{Formula (1)}$$

In formula (1), $d_i$ represents a position vector of a transducer 130$i$, r represents a position vector of the interest region 1110, v represents the sound velocity within the subject 1100, and b represents a reception signal that has been subjected to a process including differentiation processing. A sum symbol $\Sigma$ represents the sum of the transducers 1301 to 130$n$. Furthermore, ($|d_i-r|/v$) indicates a time t at which the photo acoustic waves generated in the interest region 1110 arrive at the transducer 130$i$.

Furthermore, the reception signal b which has been subjected to differentiation processing or the like is represented by formula (2).

$$b(d_i,t) = 2 \cdot p_d(d_i,t) - 2 \cdot t \cdot \partial p_d(d_i,t)/\partial t \qquad \text{Formula (2)}$$

In formula (2), p($d_i$, t) represents a value at the time t of the reception signal output by the transducer located at the position $d_i$.

Furthermore, $\Delta\Omega_i$ in formula (1) represents a weighting factor represented by formula (3).

$$\Delta\Omega_i = \frac{\Delta S_i}{|r-d_i|^2} \cdot \left[ n_{0i}^s \cdot \frac{r-d_i}{|r-d_i|} \right] = \frac{\Delta S_i}{|r-d_i|^2} \cdot \cos\theta_i \qquad \text{Formula (3)}$$

In formula (3), $n_{0i}^s$ represents a unit normal vector of a reception surface of the transducer 130$i$, $\theta_i$ represents an angle formed by a vector r–$d_i$ and the vector $n_{0i}^s$, and $\Delta S_i$ represents the area of a reception surface of the i-th transducer. That is, the weighting factor $\Delta\Omega_i$ is equal to the solid angle of a cone whose vertex is the interest region 1110 and whose bottom surface is the reception surface of the transducer 130$i$.

As described above, Non-Patent Literature 1 discloses to obtain initial sound pressure by correcting a reception signal using a weighting factor based on the solid angle formed by an interest region and a transducer.

Furthermore, Patent Literature 1 (Japanese Patent Laid-Open No. 2010-104816) discloses photo acoustic imaging that receives photo acoustic waves in a wide region of a subject by mechanically moving a transducer. However, in the case where the calculation of initial sound pressure is performed by using many reception signals obtained in the wide region of the subject, the amount of data to be handled increases, therefore it takes a long time to calculate the initial sound pressure.

Thus, Patent Literature 1 discloses a method to sequentially obtain initial sound pressures, using signals received up to the point of calculation during the scanning. Furthermore, Patent Literature 1 discloses to add a plurality of initial sound pressures obtained sequentially.

SUMMARY OF THE INVENTION

Accordingly, the present invention provides a subject information acquisition device that can reduce the time to obtain subject information such as initial sound pressure, and furthermore, that can suppress a decrease in the quantitativity of the subject information.

A subject information acquisition device according to an aspect of the present invention includes an elastic wave receiving unit configured to receive elastic waves generated inside a subject and output a reception signal; and a signal processing unit configured to acquire subject information in an interest region of the subject, on the basis of the reception signal. In a plurality of measurement states, the elastic wave receiving unit receives elastic waves and outputs a plurality of reception signals corresponding to the plurality of measurement states. The signal processing unit corrects the plurality of reception signals by a plurality of weighting factors based on a plurality of measurement parameters in the plurality of measurement states, and acquires a plurality of corrected reception signals in the interest region corresponding to the plurality of measurement states. The signal processing unit acquires the subject information in the interest region, on the basis of the sum of the plurality of corrected reception signals and the sum of the plurality of weighting factors.

Further features of the present invention will become apparent from the following description of exemplary embodiments with reference to the attached drawings.

DESCRIPTION OF THE EMBODIMENTS (Device Configuration)

Figure 1:
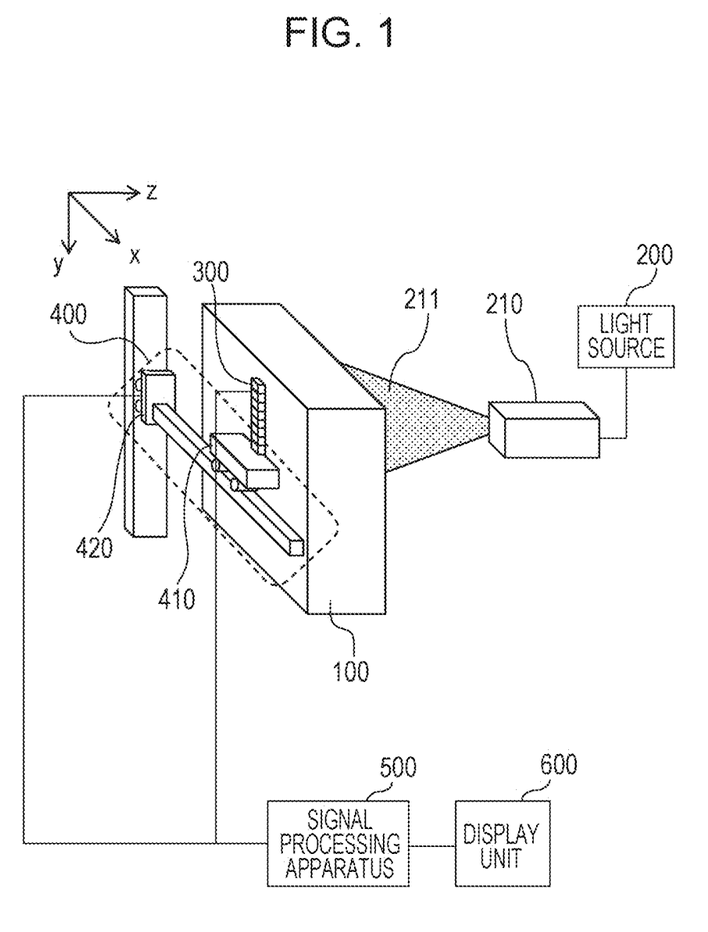
FIG. 1 is a diagram illustrating a subject information acquisition device according to an embodiment.

Firstly, with reference to FIG. 1, the device configuration of a subject information acquisition device according to an embodiment of the present invention will be explained. FIG. 1 is a diagram illustrating a subject information acquisition device according to a first embodiment.

The subject information acquisition device according to this embodiment includes a light source 200, an irradiation optical system 210, an array transducer 300 as an elastic wave receiving unit (elastic wave detector), a scanning mechanism 400 as a moving part, a signal processing apparatus 500 as a signal processing unit, and a display unit 600. The array transducer 300 according to this embodiment has one transducer arranged in a direction x and eight transducers arranged in a direction y.

The irradiation optical system 210 leads light generated by the light source 200 and irradiates a subject 100 with the light. A light absorption body within the subject 100 absorbs light energy and generates photo acoustic waves as elastic waves. The generated photo acoustic waves propagate within the subject 100 and reach the array transducer 300. The array transducer 300 receives the photo acoustic waves and outputs a reception signal to the signal processing apparatus 500. The signal processing apparatus 500 performs image reconstruction based on the reception signal, and through this obtains initial sound pressure distribution as subject information. Furthermore, the signal processing apparatus 500 generates image data from the initial sound pressure distribution, and then the image data is displayed on the display unit 600.

Furthermore, according to this embodiment, by changing measurement parameters during measurement, initial sound pressure distribution as subject information is obtained from a plurality of reception signals corresponding to a plurality of measurement states obtained by receiving photo acoustic waves in the plurality of different measurement states. The measurement state when the subject is irradiated with light will herein be defined as the measurement state.

Here, a measurement parameter used in an aspect of the present invention, represents a parameter of a measurement state which influences a weighting factor which corrects a reception signal. For example, a measurement parameter is the position of a transducer relative to an interest region, the angle formed by a reception surface of the transducer and the interest region, a transducer used to obtain subject information in the interest region, or the like. The transducer to be used corresponds to the reception signal to be used for signal processing, which will be explained more in detail later. That is, selecting a transducer to be used is equivalent to selecting a reception signal output from the transducer. Moreover, a plurality of measurement parameters may be combined together, and be considered as a measurement parameter in a measurement state.

Figure 2:
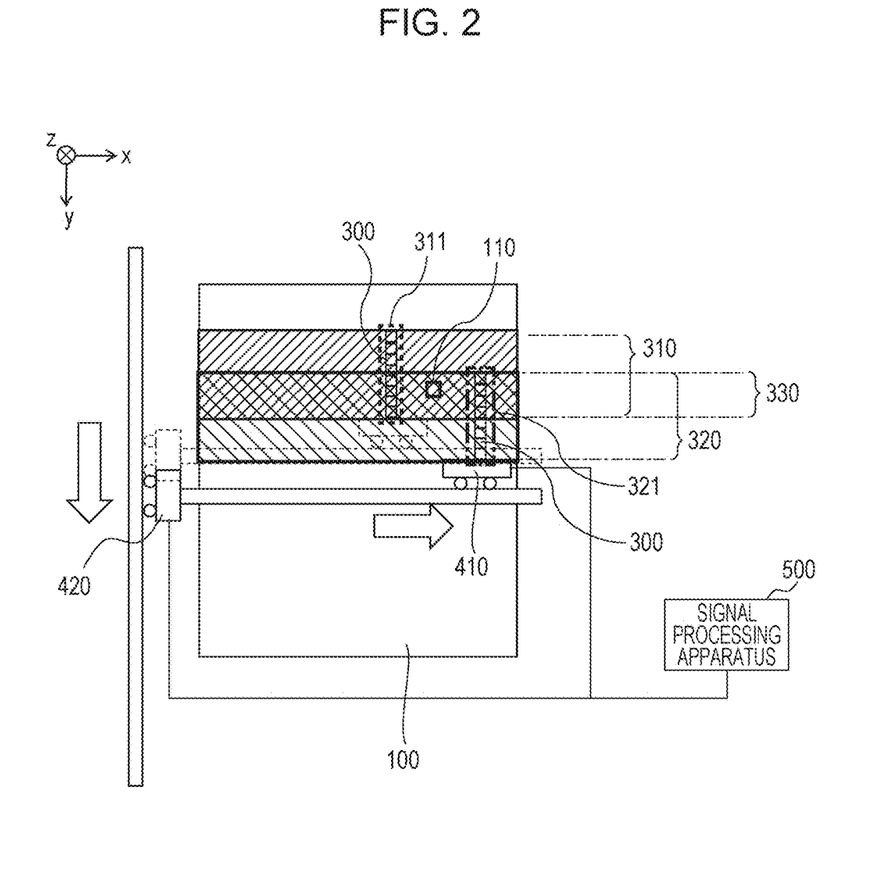
FIG. 2 is a block diagram of the subject information acquisition device illustrating a state in which an array transducer is moved to different positions.

FIG. 2 is a diagram illustrating a state in which the array transducer 300 is moved by the scanning mechanism 400 in at least two directions different from each other. The scanning mechanism 400 includes a main-scanning mechanism 410 and a sub-scanning mechanism 420. The main-scanning mechanism 410 moves the array transducer 300 along a main-scanning direction (direction x), and the sub-scanning mechanism 420 moves the array transducer 300 along a sub-scanning direction (direction y).

The main-scanning mechanism 410 moves the array transducer 300 to form a plurality of main-scanning areas. The sub-scanning mechanism 420 moves the array transducer 300 to form an overlap area 330, which is an area where an i-th main-scanning area 310 and an i+1-th main-scanning area 320 partially overlap.

According to this embodiment, the signal processing apparatus 500 is configured so that a user can set the overlap width of sub-scanning in a desired manner. Furthermore, the signal processing apparatus 500 is also configured so that the user can set main-scanning areas in a desired manner. Thus, the signal processing apparatus 500 controls the scanning mechanism 400 with a scanning pattern corresponding to the overlap width and the scanning areas set as described above.

Furthermore, the signal processing apparatus 500 may control the scanning mechanism 400 by referring to lookup tables which correspond to a plurality of specific scanning patterns stored in a non-illustrated memory of the signal processing apparatus 500.

(Subject Information Acquisition Method)

Figure 3:
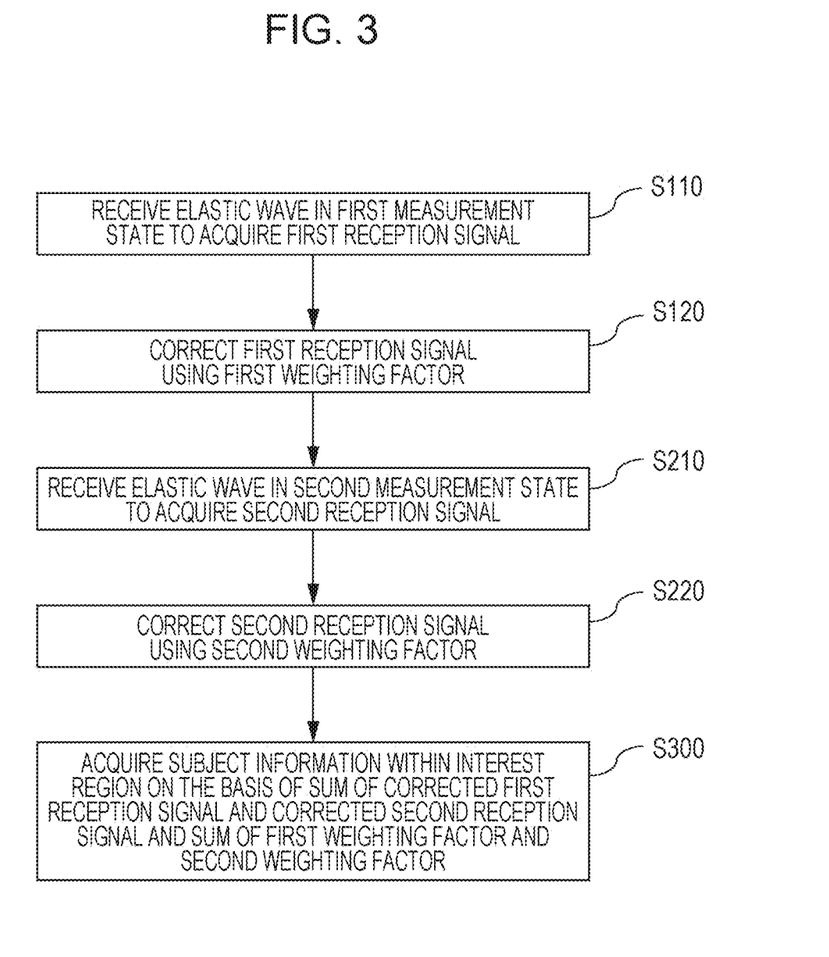
FIG. 3 is a flowchart of a subject information acquisition process according to an embodiment.

A subject information acquisition process (method) according to an embodiment will now be explained with reference to a flowchart illustrated in FIG. 3. The signal processing apparatus 500 reads a program which is stored in the memory of the signal processing apparatus 500 and in which computer-executable instructions for a subject information acquisition method is described. Based on the instructions, the signal processing apparatus 500 causes a subject information acquisition device to execute the read subject information acquisition method.

(S110: Step of Receiving Elastic Waves in a First Measurement State and Acquiring a First Reception Signal)

In step S110, the scanning mechanism 400 first moves the array transducer 300 at a first position 311. When the array transducer 300 is positioned at the first position 311, the irradiation optical system 210 leads light generated by the light source 200 and irradiates the subject 100 with irradiation light 211. The transducers 302 to 306 of the array transducer 300 are selectively used, and detect photo acoustic waves as first elastic waves to output a first reception signal $P_d^1$. The first reception signal output $p_d^1$ from the array transducer 300 is stored into the memory of the signal processing apparatus 500. In FIG. 2, the first position 311 is a specific position in the i-th main-scanning area 310 illustrated in FIG. 2. A value of the first reception signal output $p_d^1$ relating to the first position 311 is represented by a superscript "1". A value relating to a second position, which will be described later, is represented by a superscript "2", and so on.

In this embodiment, the measurement state in which the array transducer 300 can receive photo acoustic waves at the first position 311 and the measurement state in which the transducers 302 to 306 are used are defined as the first measurement state.

At this time, the signal processing apparatus 500 controls the light source 200 and the scanning mechanism 400 in synchronization with each other so that the light source 200 irradiates the subject 100 with light, and photo acoustic waves are received when the array transducer 300 is located at the first position 311.

Figure 4A:
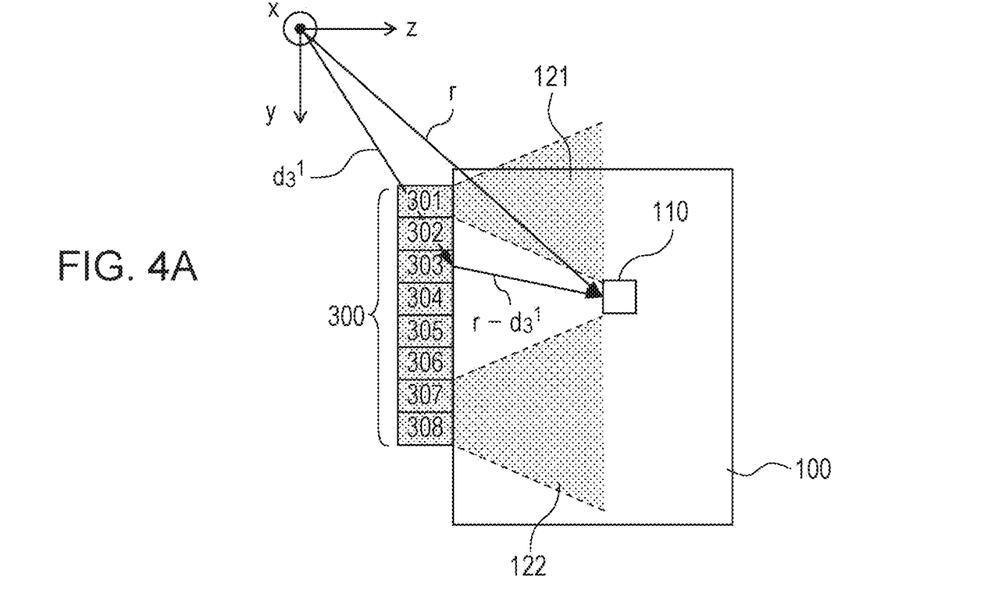
FIG. 4A is a diagram illustrating a state in which photo acoustic waves are received when an array transducer is positioned at a first position.

FIG. 4A illustrates the state in which the array transducer 300 located at the first position 311 receives photo acoustic waves generated in an interest region 110. Here, the interest region 110 is set to a specific position in the overlap area 330 illustrated in FIG. 2. In FIG. 4A, $d_3^1$ represents a position vector of the transducer 303 when the array transducer 300 is located at the first position 311.

In step S110, the transducers 302 to 306 located at the first position 311 are used. Here, a transducer to be used is determined, taking into consideration the directivity angle of the transducer. For example, in step S110, a directivity angle 121 of the transducer 301 and a directivity angle 122 of the transducers 307 to 308 do not include the interest region 110. Thus, in step S110, the transducers 301, 307, and 308 are not used, whereas, the transducers 302 to 306 are used. Here, not using a transducer includes not storing a reception signal output from the transducer into the memory or not using the reception signal stored in the memory for signal processing described later.

A transducer to be used may be determined, taking into consideration attenuation of photo acoustic waves, as well as directivity angle. That is, a transducer to be used may be determined on the basis of the distance between an interest region and the transducer.

Furthermore, as described in Patent Literature 1, the sum of a plurality of reception signals acquired a plurality of times at the same position may be used as a reception signal at the position.

Furthermore, after performing a process, such as multiplication processing, division processing, filtering processing, differentiation processing, envelope detection processing, logarithmic compression processing, or orthogonal detection processing, on a reception signal, the signal processing apparatus 500 may store the processed reception signal into the memory. Alternatively, after storing a reception signal into the memory, the signal processing mentioned above may be performed on the reception signal stored in the memory. A reception signal used in an aspect of the present invention includes a reception signal that has been subjected to the above-mentioned signal processing.

In the case where a photo acoustic imaging device is employed as a subject information acquisition device, it is preferable that a process including differentiation processing is performed on a reception signal, as represented by formula (2).

(S120: Step of Correcting the First Reception Signal by a First Weighting Factor)

In step S120, the signal processing apparatus 500 corrects the first reception signal corresponding to the first measurement state acquired in step S110 by a first weighting factor. The first reception signal corrected by the first weighting factor is stored into the memory of the signal processing apparatus 500.

The first reception signal corresponding to the interest region 110 is a reception signal acquired at a time when photo acoustic waves generated in the interest region 110 are received by a transducer at the first position 311, among reception signals acquired in time series. That is, in this embodiment, the reception signal corresponding to the interest region 110 is a reception signal obtained at the time t, which is a value obtained by dividing the distance $(d_i - r)$ between a transducer and the interest region 110 by sonic speed v, where the time $t_0$ at which irradiation with light is performed is set to 0.

Furthermore, a value determined based on a measurement parameter in a measurement state and the position of an interest region is used as a weighting factor. In this embodiment, as disclosed in Non-Patent Literature 1, the solid angle $\Delta\Omega$ of a cone whose vertex is defined by the interest region 110 and whose bottom surface is defined by the reception surface of the array transducer 300 is used as a weighting factor.

In step S120, the signal processing apparatus 500 calculates a first weighting factor $\Delta\Omega^1$ corresponding to the transducers 302 to 306 using formula (3), on the basis of the position of the first position 311 and the position of the interest region 110. The signal processing apparatus 500 corrects the first reception signal corresponding to the interest region 110 by the first weighting factor. Formula (4) represents a corrected first reception signal $P_c^1(r)$ corresponding to the interest region 110.

$$P_C^1(r) = \sum_{i=2}^{6} \Delta\Omega_i^1 \times P_{di}^1\left(d_i^1, \frac{|d_i^1|}{v}\right) \qquad \text{Formula (4)}$$

In step S120, the signal processing apparatus 500 calculates the corrected first reception signal represented by formula (4) by multiplying first reception signals acquired by individual transducers corresponding to the interest region 110 by the first weighting factor.

In the case where a scanning pattern is set on the basis of a lookup table, the signal processing apparatus 500 may acquire a weighting factor on the basis of a specific scanning pattern corresponding to a selected lookup table. Alternatively, the signal processing apparatus 500 may acquire a weighting factor by referring to a lookup table in which a weighting factor corresponding to a set scanning pattern is stored.

Furthermore, in the case where the array transducer 300 receives photo acoustic waves as in this embodiment, a plurality of reception signals acquired by transducers of the array transducer 300 located at the first position 311 may be collectively called a "first reception signal".

Furthermore, a plurality of reception signals acquired at different positions by one or more transducers may also be collectively called a "first reception signal". In this case, a plurality of positions at which photo acoustic waves are received are collectively called a "first position".

For example, the case where all the reception signals acquired by the array transducer 300 by the i-th main-scanning are collectively called a "first reception signal" will be considered. In this case, the scanning areas 310 scanned by the i-th main-scanning are collectively called a "first position".

(S210: Step of Receiving Elastic Waves in a Second Measurement State and Acquiring a Second Reception Signal)

In step S210, the scanning mechanism 400 first scans the array transducer 300 at a second position 321. When the array transducer 300 is located at the second position 321, the irradiation optical system 210 leads light generated by the light source 200 and irradiates the subject 100 with the irradiation light 211. The transducers 301 to 304 of the array transducer 300 are selectively used, and detect photo acoustic waves as second elastic waves to output a second reception signal $P_d^2$. The second signal output from the array transducer 300 is stored into the memory of the signal processing apparatus 500.

The second position 321 represents a specific position in the i+1-th main-scanning area 320 illustrated in FIG. 2.

At this time, the signal processing apparatus 500 controls the light source 200 and the scanning mechanism 400 in synchronization with each other so that the light source 200 irradiates the subject 100 with light and photo acoustic waves are received when the array transducer 300 is located at the second position 321.

Figure 4B:
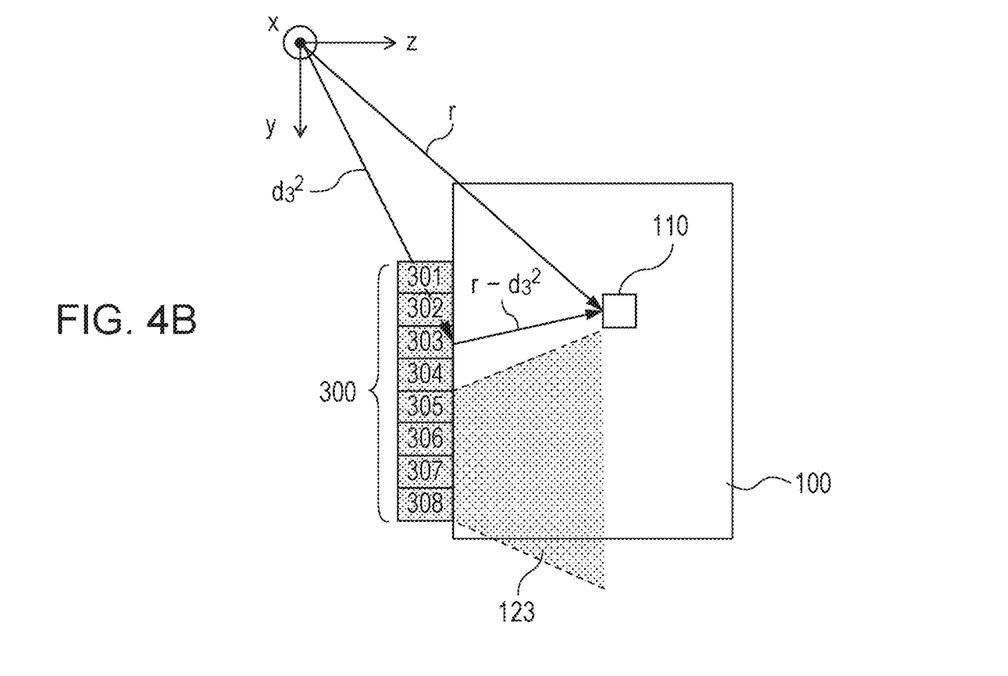
FIG. 4B is a diagram illustrating a state in which photo acoustic waves are received when an array transducer is positioned at a second position.

FIG. 4B illustrates the state in which the array transducer 300 located at the second position 321 receives photo acoustic waves generated in the interest region 110. In FIG. 4B, $d_3^2$ represents a position vector of the transducer 303 when the array transducer 300 is located at the second position 321.

Similar to step S110, the signal processing apparatus 500 determines a transducer to be used, on the basis of the directivity angle of the transducer, in step S210. In step S210, since a directivity angle 123 of the transducers 305 to 308 does not include the interest region 110, only the transducers 301 to 304 are used.

(S220: Step of Correcting the Second Reception Signal by a Second Weighting Factor)

In step S220, the signal processing apparatus 500 corrects the second reception signal corresponding to the interest region 110 acquired in step S210 by a second weighting factor. The second reception signal corrected by the second weighting factor is stored into the memory of the signal processing apparatus 500.

In this embodiment, the signal processing apparatus 500 acquires a second weighting factor $\Delta\Omega^2$ corresponding to the transducers 301 to 304 using formula (3) on the basis of the second position 321 of the array transducer 300 and the position of the interest region 110. Then, the signal processing apparatus 500 calculates a corrected second reception signal by multiplying the second reception signal corresponding to the interest region 110 acquired in step S210 by the second weighting factor.

Then, the signal processing apparatus 500 multiplies the second reception signal in the interest region 110 by the second weighting factor to calculate a corrected second reception signal in the interest region 110. Formula (5) represents the corrected second reception signal $P_c^2(r)$ in the interest region 110.

$$P_C^2(r) = \sum_{i=1}^{4} \Delta\Omega_i^2 \times P_{di}^2\left(d_i^2, \frac{|d_i^2 - r|}{v}\right) \quad \text{Formula (5)}$$

The signal processing apparatus 500 may correct the first reception signal and the second reception signal by weighting factors and acquire the sum of the corrected reception signals as a corrected second reception signal in the interest region 110, as represented by formula (6).

$$P_C^2(r) = \sum_{i=2}^{6} \Delta\Omega_i^1 \times P_{di}^1\left(d_i^1, \frac{|d_i^1 - r|}{v}\right) + \sum_{i=1}^{4} \Delta\Omega_i^2 \times P_{di}^2\left(d_i^2, \frac{|d_i^2 - r|}{v}\right) \quad \text{Formula (6)}$$

Preferably, step S120 is performed prior to step S220. As described above, by performing step S220 after completing step S120 by the signal processing apparatus 500, the time at which both steps S120 and S220 are completed can be made earlier than the case where steps S120 and S220 are performed at the same time. That is, the time required to acquire subject information can be shortened.

(S300: Step of Acquiring Subject Information in the Interest Region on the Basis of the Sum of the Corrected First Reception Signal and the Corrected Second Reception Signal and the Sum of the First Weighting Factor and the Second Weighting Factor)

In step S300, the signal processing apparatus 500 acquires initial sound pressure as subject information in the interest region, on the basis of the sum of the corrected first reception signal acquired in step S120 and the corrected second reception signal acquired in step S220 and the sum of the first weighting factor and the second weighting factor.

In step S300, the signal processing apparatus 500 calculates initial sound pressure $P_0$ in an interest region by dividing the sum of the corrected first reception signal and the corrected second reception signal by the sum of the first weighting factor and the second weighting factor, as represented by formula (7).

$$p_0(r) = \frac{\sum_{i=2}^{6} \Delta\Omega_i^1 \times P_{di}^1\left(d_i^1, \frac{|d_i^1 - r|}{v}\right) + \sum_{i=1}^{4} \Delta\Omega_i^2 \times P_{di}^2\left(d_i^2, \frac{|d_i^2 - r|}{v}\right)}{\sum_{i=2}^{6} \Delta\Omega_i^1 + \sum_{i=1}^{4} \Delta\Omega_i^2} \quad \text{Formula (7)}$$

The numerator of formula (7) is the sum of the corrected first reception signal represented by formula (4) and the corrected second reception signal represented by formula (5). The denominator of formula (7) is the sum of the first weighting factor and the second weighting factor.

As described above, by dividing the corrected first reception signal and the corrected second reception signal by the same value (the sum of the first weighting factor and the second weighting factor), the quantitativity of the initial sound pressure obtained at each point increases.

For example, in the case where the reciprocal of initial sound pressure is obtained as subject information, the signal processing apparatus 500 may divide the sum of the first weighting factor and the second weighting factor by the sum of the corrected first reception signal and the corrected second reception signal.

That is, either in the case where initial sound pressure is obtained or in the case where the reciprocal of initial sound pressure is obtained, the signal processing apparatus 500 may acquire the ratio of the sum of the first weighting factor and the second weighting factor to the sum of the corrected first reception signal and the corrected second reception signal.

Furthermore, the signal processing apparatus 500 may acquire the light amount distribution within a subject in each measurement state. Furthermore, for example, by dividing the initial sound pressure in an interest region acquired in step S300 by the light amount value in the interest region, the signal processing apparatus 500 can acquire an absorption coefficient in the interest region. At this time, the signal processing apparatus 500 may use the average of a plurality of light amount values corresponding to measurement states for acquisition of the absorption coefficient. Furthermore, the signal processing apparatus 500 is capable of acquiring substance concentration distribution, such as the degree of oxygen saturation, on the basis of absorption coefficients in the interest region acquired by light of a plurality of wavelengths.

The present invention may also be applied to an aspect in which subject information is acquired from corrected reception signals acquired at three or more positions.

Furthermore, although a photo acoustic imaging device that acquires subject information by receiving photo acoustic waves has been explained in this embodiment, the present invention can also be applied to an ultrasound diagnosis device that acquires subject information by transmitting and receiving ultrasonic waves. The present invention can be applied to various devices that receive elastic waves and correct a reception signal using a weighting factor to acquire subject information. That is, elastic waves used in an aspect of the present invention include photo acoustic waves generated by a photo acoustic effect and reflected waves of transmitted ultrasonic waves.

For example, in an ultrasound diagnosis device according to an aspect of the present invention, an array transducer functioning as an ultrasonic wave transmitter first transmits ultrasonic waves to a subject, and the array transducer functioning as an ultrasonic wave receiver receives ultrasonic waves reflected inside the subject and outputs a reception signal. At this time, the array transducer transmits and receives ultrasonic waves while changing a measurement parameter in each of a plurality of measurement states. A measurement parameter used in an ultrasound diagnosis device may be the position of an ultrasonic wave receiver, the number of transducers used, the direction in which ultrasonic waves are transmitted, or the like. Here, a transducer used represents a transducer corresponding to a reception signal to be used later in signal processing. Furthermore, in an ultrasound diagnosis device, it is preferable that an array transducer performs transmission focusing and reception focusing and outputs a reception signal. Alternatively, the array transducer may transmit plane ultrasonic waves and receive reflected waves of the plane ultrasonic waves.

Then, a signal processing device corrects reception signals in measurement states using weighting factors based on measurement parameters in the measurement states and the position of an interest region. Then, the signal processing device acquires structural information of the subject as subject information, on the basis of the sum of corrected reception signals and the sum of weighting factors.

Structural information is information based on the photo acoustic impedance distribution within a subject. For example, structural information may be a B-mode image, a Doppler image, or an elastographic image that can be obtained by known ultrasound diagnosis devices.

The subject information acquisition method described above may be configured as a program that causes the signal processing apparatus 500 as a computer to execute to the subject information acquisition method.

(Effects of Embodiment)

Figure 5:
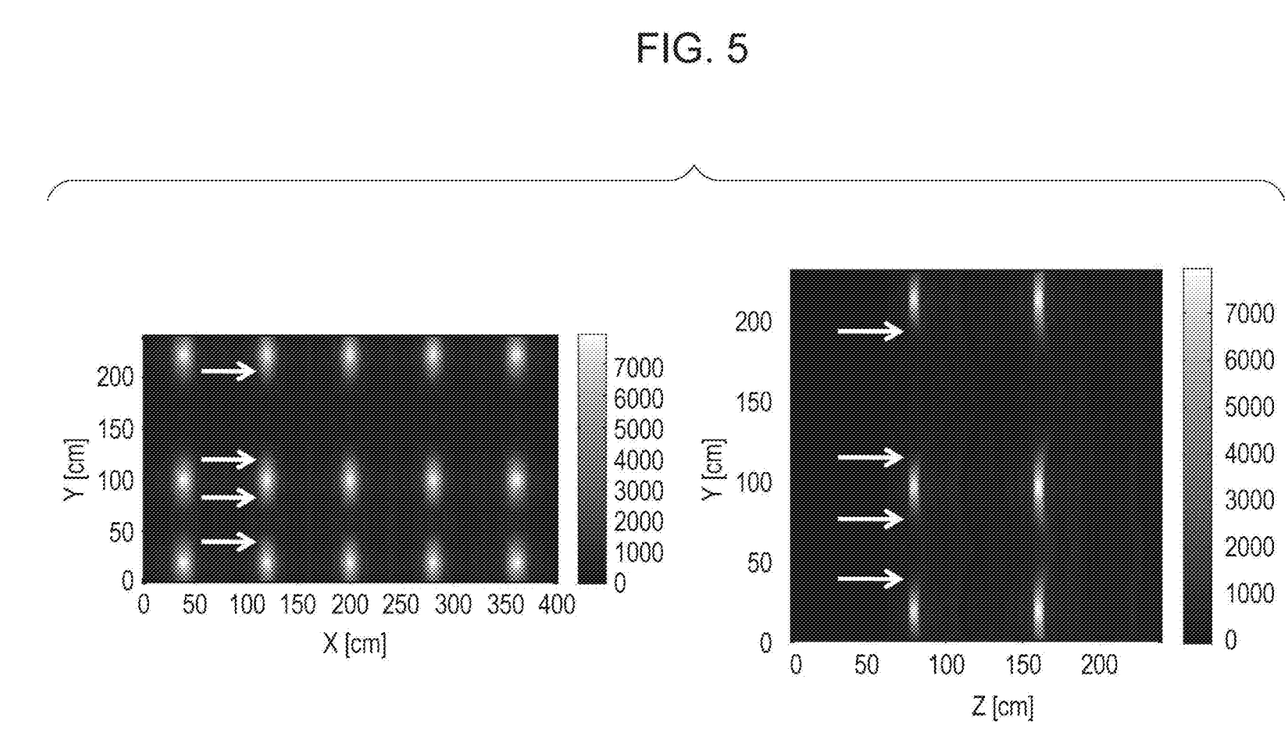
FIG. 5 illustrates initial sound pressure distribution obtained with a subject information acquisition device, in accordance in an exemplary embodiment of the present invention.

FIG. 5 illustrates initial sound pressure distribution within a subject acquired by the subject information acquisition method according to this embodiment.

In this embodiment, by performing main-scanning in the direction x and sub-scanning in the direction y on the array transducer, a reception signal is acquired. The array transducer is moved in a sub-scanning direction (sub-scanned) in such a manner that main-scanning areas overlap in regions represented by arrows.

A corrected reception signal in a region in a direction z of a scanning area (region facing in front of the array transducer) is acquired for each main-scanning operation.

In the region in the direction z of overlapping scanning areas, initial sound pressure is acquired by dividing the sum of the corrected reception signals by the sum of weighting factors corresponding to the overlapping scanning areas, as in formula (7). In contrast, in the other regions, initial sound pressure is acquired as in formulae (4) and (5).

As described above, in the region in the direction z of the overlapping scanning areas, since the initial sound pressure is acquired by the subject information acquisition method according to this embodiment, a high quantitativity is achieved. As a result, the continuity of the initial sound pressure distribution in this embodiment illustrated in FIG. 5 is higher than the continuity of the initial sound pressure distribution in a comparative example illustrated in FIG. 6, which will be described later.

(Comparative Example)

In contrast, the case where initial sound pressures are sequentially acquired as disclosed in Patent Literature 1 using the method for acquiring initial sound pressure disclosed in Non-Patent Literature 1 and the average of the initial sound pressures is obtained, will be considered as a comparative example.

For example, the case in which a signal processing apparatus acquires an initial sound pressure $P_0(r)$ in an interest region by obtaining the average of an initial sound pressure $P_0^1$ based on a reception signal acquired at the first position 311 and an initial sound pressure $p_0^2$ based on a reception signal acquired at the second position 321 will be considered.

At this time, the initial sound pressure acquired in the comparative example is represented by formula (8), with reference to formula (1). It is assumed that also in the comparative example, a reception signal is acquired in a manner similar to this embodiment.

$$p_0(r) = \frac{p_0^1(r) + p_0^2(r)}{2} = \frac{\frac{\sum_{i=2}^{6} \Delta\Omega_i^1 \times P_{di}^1\left(d_i^1, \frac{|d_i^1 - r|}{v}\right)}{\sum_{i=2}^{6} \Delta\Omega_i^1} + \frac{\sum_{i=1}^{4} \Delta\Omega_i^2 \times P_{di}^2\left(d_i^2, \frac{|d_i^2 - r|}{v}\right)}{\sum_{i=1}^{4} \Delta\Omega_i^2}}{2}$$ Formula (8)

As represented by formula (8), initial sound pressures represented as terms of the numerator are acquired by dividing corrected reception signals by different weighting factors. Thus, the quantitativity of the initial sound pressure obtained by averaging initial sound pressures acquired using different weighting factors may be decreased.

Figure 6:
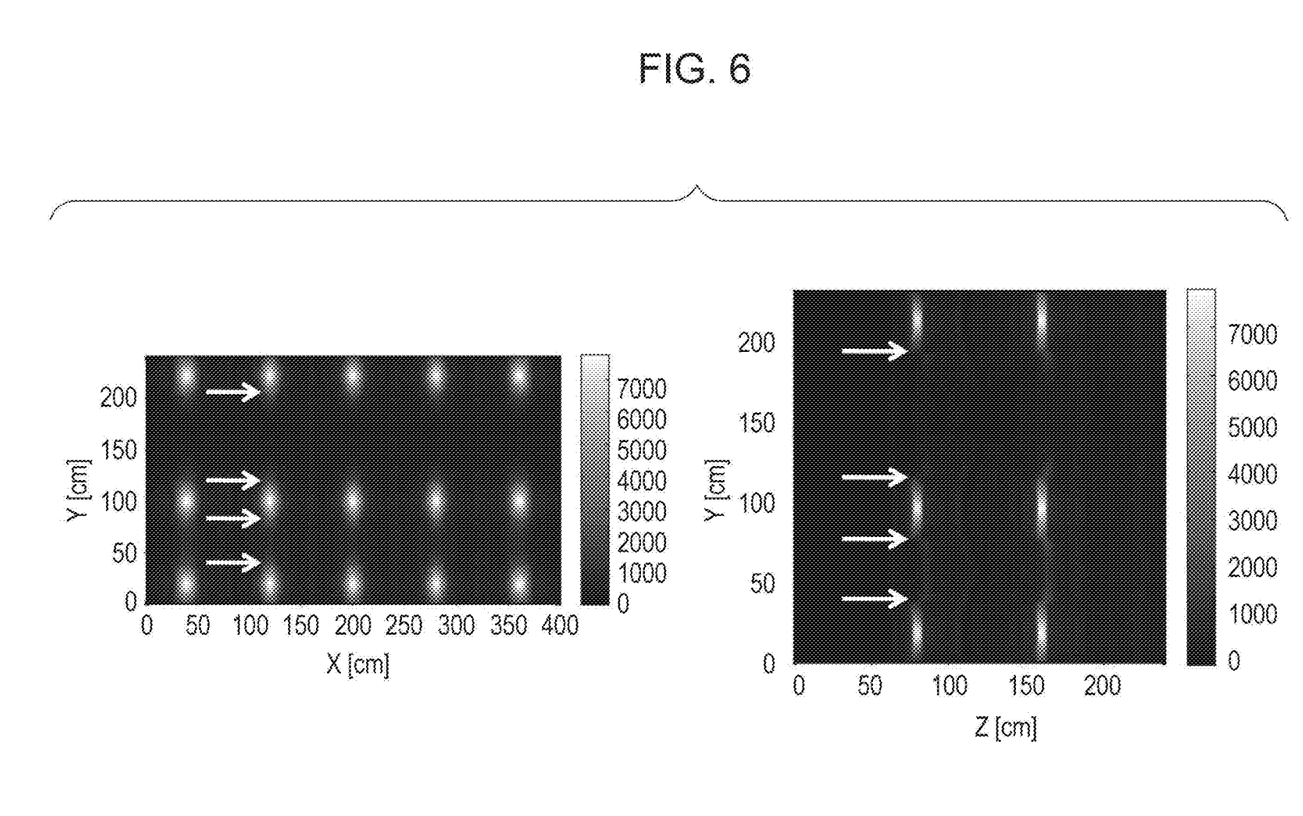
FIG. 6 illustrates initial sound pressure distribution obtained in a comparative example.

FIG. 6 illustrates the initial sound pressure distribution of a subject in the comparative example. The array transducer is sub-scanned in such a manner that scanning areas overlap in regions represented by arrows. The positions of the arrows in FIG. 6 are equal to the positions of the arrows in FIG. 5.

In the comparative example, the initial sound pressure in the direction z of a scanning area is acquired for each main-scanning operation, using formula (1). For a region in the direction z of overlapping scanning areas, the initial sound pressure distribution is acquired by averaging initial sound pressures obtained by main-scanning operations, as in formula (8).

In the case where the average of initial sound pressures obtained by different weighting factors for main-scanning operations is obtained as described above, the quantitativity of initial sound pressure may decrease. Thus, at the positions indicated by the arrows in FIG. 6, continuity of the initial sound pressure distribution is decreased compared to the initial sound pressure distribution illustrated in FIG. 5.

(Basic Configuration)

Hereinafter, the principal configuration of the subject information acquisition device according to this embodiment will be explained.

(Light Source 200)

Preferably, in order to achieve a photo acoustic effect, the pulse width of light generated by the light source 200 is several hundred nanoseconds or less. Furthermore, for measurement of breast cancer or the like, it is preferable that light having a specific wavelength absorbed by a specific component (for example, hemoglobin) of components constituting a living body is generated. Although it is preferable to use a laser capable of realizing large output as a light source, a light-emitting diode or the like may be used instead of a laser. Various lasers, such as a solid-state laser, a gas laser, a dye laser, or a semiconductor laser, may be used.

(Irradiation Optical System 210)

The irradiation optical system 210 leads light generated by the light source 200 and irradiates the subject 100 with the irradiation light 211 using a method appropriate for photo acoustic measurement.

Figure 7:
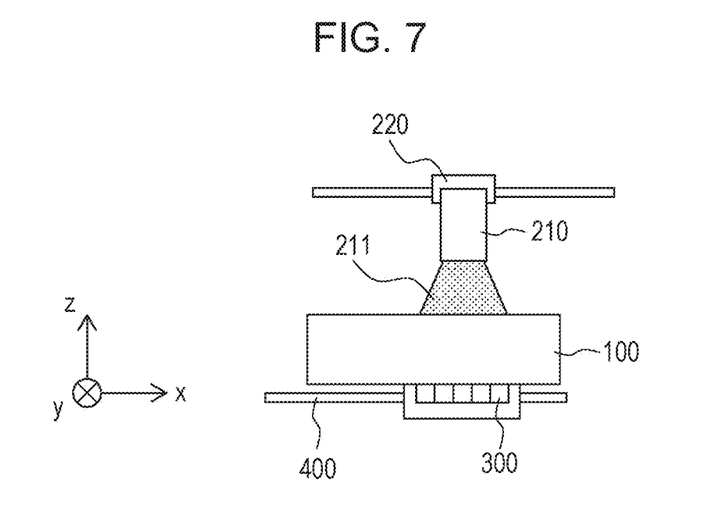
FIG. 7 is a diagram illustrating an irradiation optical system according to an embodiment.

The irradiation optical system 210 may be configured so as to be moved by an optical scanning mechanism 220, as illustrated in FIG. 7. With this configuration, even in the case where an irradiation area of the irradiation light 211 is narrow, a wide area of the subject 100 can be irradiated with the irradiation light 211 by moving the irradiation optical system 210. Furthermore, the irradiation optical system 210 may irradiate the entire measurement region including the subject 100 at a time.

Since the intensity of photo acoustic waves is proportional to the intensity of light, the irradiation optical system 210 preferably concentrates light energy of the irradiation light 211.

In order to increase the signal-to-noise (SN) ratio of a reception signal, the irradiation optical system 210 may allow irradiation not only through one surface but also through a plurality of surfaces of the subject 100. For example, the irradiation optical system 210 may be configured to allow irradiation not only through a surface that is in contact with the array transducer 300 but also through a surface that is opposite the array transducer 300.

The irradiation optical system 210 may include a mirror, a light-collecting lens, a magnifying lens, a shape-changing lens, a prism that diffuses, refracts, and reflects light, or one or more optical fibers. Any other optical components may be used as long as they can irradiate the subject 100 with light generate by a light source in a desired manner (irradiation direction, irradiation field, form, or the like).

(Array Transducer 300)

The array transducer 300 receives elastic waves and converts the elastic waves into an electric signal. Transducers forming the array transducer 300 may be transducers using a piezoelectric phenomenon, transducers using resonance of light, transducers using a change in capacitance, or the like. Any type of transducer may be used as long as it can receive elastic waves and convert the elastic waves into an electric signal.

With the use of an array transducer 300 including a plurality of transducers, elastic waves can be received at different positions by a single receiving operation. Thus, compared to the case in which a single transducer is used, the measurement time can be shortened. Furthermore, the direction in which the reception sensitivity is high of at least one element of a plurality of transducers may be directed toward a specific region. Normally, the direction of a normal of the reception surface of a transducer is equal to the direction in which the reception sensitivity is high. For example, as described in Patent Document 2 (U.S. Pat. No. 5,713,356), a plurality of transducers may be arranged in a spiral shape on a hemispheric base.

However, in an aspect of the present invention, elastic waves may be received using a single transducer, instead of using a plurality of transducers.

(Scanning Mechanism 400)

The scanning mechanism 400 is a mechanism that moves the array transducer 300. With the scanning mechanism 400, the array transducer 300 is capable of receiving elastic waves at different positions.

In the case where the irradiation optical system 210 is scanned with the optical scanning mechanism 220, it is preferable that scanning of the irradiation optical system 210 and scanning of the array transducer 300 are performed in synchronization with each other. In addition, it is further preferable that the timing at which irradiation with the irradiation light 211 is performed and the timing at which the array transducer 300 receives photo acoustic waves are in synchronization with each other.

As illustrated in FIG. 1, the scanning mechanism 400 moves the array transducer 300 two-dimensionally. However, movement of the array transducer 300 is not limited to being two-dimensional. The scanning mechanism 400 may move the array transducer 300 three-dimensionally so as to translate and rotate around a subject.

A moving part used in an aspect of the present invention may be a mechanical moving part like the scanning mechanism 400 according to this embodiment or may be a holding part held by a user so that the user can cause the array transducer 300 to be moved.

(Signal Processing Apparatus 500)

Preferably, the signal processing apparatus 500 amplifies a reception signal output from the array transducer 300 and converts the reception signal from an analog signal into a digital signal. As used herein, a "reception signal" includes an analog signal output from the array transducer 300 and a digital signal that is analog-to-digital converted by the signal processing apparatus 500.

The signal processing apparatus 500 acquires an optical characteristic value inside a subject as subject information by performing image reconstruction or the like. Typically, a workstation including one or more microprocessors, or the like, is used as the signal processing apparatus 500. Image reconstruction processing and control of the subject information acquisition device is performed by software programmed in advance and executed by the one or more microprocessors. For example, time-domain back projection is performed as image reconstruction processing by the signal processing apparatus 500, based on known algorithms. Similarly, a subject information acquisition process is performed by the signal processing apparatus 500, based on the algorithm illustrated in FIG. 3, for example.

Here, subject information used in an aspect of the present invention is data representing information inside a subject, regardless of whether the data is two-dimensional or three-dimensional. In a subject information acquisition device using a photo acoustic effect, subject information is initial sound pressure distribution, light absorption coefficient distribution, oxygen saturation degree distribution, or the like inside a subject. In a subject information acquisition device using reflected waves of ultrasonic waves, subject information is acoustic impedance distribution, elastic coefficient distribution, or the like inside a subject.

Furthermore, subject information is configured such that a plurality of pixels, which are the minimum elements, are arranged in the case where the subject information is two-dimensional and that a plurality of voxels, which are the minimum elements, are arranged in the case where the subject information is three-dimensional.

The signal processing apparatus 500 generates image data by performing processing, such as luminance conversion, on acquired subject information, and outputs the generated image data to the display unit 600. The signal processing apparatus 500 may output the value of subject information in a specific position or region to the display unit 600 and may display the value of the subject information in the specific position or region on the display unit 600.

Functions of the signal processing apparatus 500 according to this embodiment may be provided as independent devices or modules.

In the case where a module is configured to be hardware, the module may be configured to be a field programmable gate array (FPGA), an application specific integrated circuit (ASIC), or the like. Modules may be configured to be programs that cause a computer to execute corresponding processes.

(Display Unit 600)

The display unit 600 displays image information and numerical information of subject information generated by the signal processing apparatus 500. For example, a liquid crystal display or the like may be used as the display unit 600. The display unit 600 may be provided independent of a subject information acquisition device according to this embodiment.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-Ray Disc (BD)™), a flash memory device, a memory card, and the like.

Although preferred embodiments of the present invention have been explained above, the present invention is not limited to the foregoing embodiments. The present invention includes various modifications and applications without departing from the scope of the claims.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. An apparatus, comprising:
   a memory configured to store a plurality of first reception signals acquired by receiving, with transducers and at a plurality of first reception positions, a first elastic wave generated by irradiating a subject with light;
   a signal processing unit configured to acquire subject information of an interest region using the plurality of first reception signals,
   wherein the signal processing unit is configured to:
      determine first signals from among the plurality of first reception signals, the first signals including reception signals corresponding to first transducers with a directivity angle including the interest region and excluding reception signals corresponding to second transducers with a directivity angle not including the interest region,
      acquire first corrected signals by correcting the first signals with first weighting factors; and
      acquire a first sum of the first corrected signals and a second sum of the first weighting factors,
   wherein the memory is configured to individually store the first sum and the second sum, and wherein the signal processing unit is configured to acquire the subject information of the interest region, by using the first sum and the second sum which are read out from the memory.

2. The apparatus according to claim 1,
wherein the memory is configured to store a plurality of second reception signals acquired by receiving, with the transducers and at a plurality of second reception positions different from the plurality of first reception positions, a second elastic wave generated by irradiating the subject with light at a timing different from the first elastic wave,
wherein the signal processing unit is configured to:
determine second signals from among the plurality of second reception signals, the second signals including reception signals corresponding to third transducers with a directivity angle including the interest region and excluding reception signals corresponding to fourth transducers with a directivity angle not including the interest region;
acquire second corrected signals by correcting the second signals with second weighting factors;
acquire a third sum of the second corrected signals and the first sum which is read out from the memory, and
acquire a fourth sum of the second weighting factors and the second sum which is read out from the memory,
wherein the memory is configured to individually store the third sum and the fourth sum; and
wherein the signal processing unit is configured to acquire the subject information of the interest region, by using the third sum and the fourth sum which are read out from the memory.

3. The apparatus according to claim 2, wherein the plurality of first reception positions and the plurality of second reception positions partially overlap each other.

4. The apparatus according to claim 2, wherein the plurality of first reception positions and the plurality of second reception positions are arranged on a same plane.

5. The apparatus according to claim 1,
wherein the memory is configured to store a plurality of second reception signals acquired by receiving, with the transducers and at a plurality of second reception positions different from the plurality of first reception positions, a second elastic wave generated by irradiating the subject with light at a timing different from the first elastic wave,
wherein the signal processing unit is configured to:
determine second signals from among the plurality of second reception signals, the second signals including reception signals corresponding to third transducers with a directivity angle including the interest region and excluding reception signals corresponding to fourth transducers with a directivity angle not including the interest region;
acquire second corrected signals by correcting the second signals with second weighting factors;
acquire a third sum of the second corrected signals, and acquire a fourth sum of the second weighting factors,
wherein the memory is configured to individually store the third sum and the fourth sum, and
wherein the signal processing unit is configured to acquire the subject information of the interest region, by using the first sum, the second sum, the third sum, and the fourth sum which are read out from the memory.

6. The apparatus according to claim 5, wherein the plurality of first reception positions and the plurality of second reception positions partially overlap each other.

7. The apparatus according to claim 5, wherein the plurality of first reception positions and the plurality of second reception positions are arranged on a same plane.

8. The apparatus according to claim 1, wherein the signal processing unit is configured to acquire the subject information of the interest region by acquiring a ratio of the first sum to the second sum.

9. The apparatus according to claim 1, wherein the first weighting factors are each a factor based on a solid angle of a cone whose vertex is the interest region and whose bottom surface is a reception surface of one or more transducers located at one of the plurality of first reception positions.

10. The apparatus according to claim 1, wherein the first weighting factors are each a factor based on a solid angle of a cone whose vertex is the interest region and whose bottom surface is a reception surface of the transducers.

11. The apparatus according to claim 1, further comprising the transducers,
wherein the transducers are arranged in such a manner that a direction in which reception sensitivity is high of at least one element of transducers is directed toward the interest region.

12. The apparatus according to claim 1, wherein the signal processing unit is configured to perform a process including differentiation processing on the first signals and correct, using the first weighting factors, the first signals that have been subjected to the differentiation processing.

13. The apparatus according to claim 1, wherein the signal processing unit is configured to acquire an initial sound pressure as the subject information.

14. The apparatus according to claim 1,
wherein the signal processing unit is configured to:
acquire an initial sound pressure of the interest region, by using the first sum and the second sum which are read out from the memory,
acquire a light amount of light, of the interest region, with which the subject is irradiated, and
acquire an absorption coefficient of the interest region as the subject information, by using the initial sound pressure of the interest region and the light amount of the interest region.

15. A signal processing method comprising:
storing a plurality of first reception signals acquired by receiving, with transducers and at a plurality of first reception positions, a first elastic wave generated by irradiating a subject with light;
acquiring subject information of an interest region using the plurality of first reception signals,
determining first signals from among the plurality of first reception signals, the first signals including reception signals corresponding to first transducers with a directivity angle including the interest region and excluding reception signals corresponding to second transducers with a directivity angle not including the interest region,
acquiring first corrected signals by correcting the first signals with first weighting factors;
acquiring a first sum of the first corrected signals and a second sum of the first weighting factors;
individually storing the first sum and the second sum, and
acquiring the subject information of the interest region, by using the first sum and the second sum which are stored.

16. The signal processing method according to claim 15, further comprising:
- storing a plurality of second reception signals acquired by receiving, with the transducers and at a plurality of second reception positions different from the plurality of first reception positions, a second elastic wave generated by irradiating the subject with light at a timing different from the first elastic wave,
- determining second signals from among the plurality of second reception signals, the second signals including reception signals corresponding to third transducers with a directivity angle including the interest region and excluding reception signals corresponding to fourth transducers with a directivity angle not including the interest region;
- acquiring second corrected signals by correcting the second signals with second weighting factors;
- acquiring a third sum of the second corrected signals and the first sum which is stored,
- acquiring a fourth sum of the second weighting factors and the second sum which is stored,
- individually storing the third sum and the fourth sum; and
- acquiring the subject information of the interest region, by using the third sum and the fourth sum which are stored.

17. The signal processing method according to claim 15, further comprising:
- storing a plurality of second reception signals acquired by receiving, with the transducers and at a plurality of second reception positions different from the plurality of first reception positions, a second elastic wave generated by irradiating the subject with light at a timing different from the first elastic wave,
- determining second signals from among the plurality of second reception signals, the second signals including reception signals corresponding to third transducers with a directivity angle including the interest region and excluding reception signals corresponding to fourth transducers with a directivity angle not including the interest region;
- acquiring second corrected signals by correcting the second signals with second weighting factors;
- acquiring a third sum of the second corrected signals,
- acquiring a fourth sum of the second weighting factors,
- individually storing the third sum and the fourth sum, and
- acquiring the subject information of the interest region, by using the first sum, the second sum, the third sum, and the fourth sum which are stored.

18. A non-transitory computer-readable storage medium storing a program that causes a computer to execute following steps:
- storing a plurality of first reception signals acquired by receiving, with transducers and at a plurality of first reception positions, a first elastic wave generated by irradiating a subject with light;
- acquiring subject information of an interest region using the plurality of first reception signals,
- determining first signals from among the plurality of first reception signals, the first signals including reception signals corresponding to first transducers with a directivity angle including the interest region and excluding reception signals corresponding to second transducers with a directivity angle not including the interest region,
- acquiring first corrected signals by correcting the first signals with first weighting factors;
- acquiring a first sum of the first corrected signals and a second sum of the first weighting factors;
- individually storing the first sum and the second sum, and
- acquiring the subject information of the interest region, by using the first sum and the second sum which are stored.

* * * * *